(12) United States Patent
Ramani et al.

(10) Patent No.: US 7,659,975 B1
(45) Date of Patent: Feb. 9, 2010

(54) METHODS AND SYSTEMS FOR INSPECTION OF A WAFER OR SETTING UP AN INSPECTION PROCESS

(75) Inventors: Vijay Ramani, Palo Alto, CA (US); Koki Mochizuki, San Jose, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 267 days.

(21) Appl. No.: 11/533,079

(22) Filed: Sep. 19, 2006

Related U.S. Application Data

(60) Provisional application No. 60/719,078, filed on Sep. 21, 2005.

(51) Int. Cl.
 *G01N 21/00* (2006.01)
(52) U.S. Cl. .................................................. 356/237.4
(58) Field of Classification Search .... 356/237.4–237.5
 See application file for complete search history.

(56) References Cited

U.S. PATENT DOCUMENTS

| | | | |
|---|---|---|---|
| 5,960,107 A * | 9/1999 | Leroux ...................... 382/145 |
| 5,991,699 A | 11/1999 | Kulkarni et al. |
| 6,590,409 B1 * | 7/2003 | Hsiung et al. ................ 324/765 |
| 6,646,735 B2 * | 11/2003 | Fukazawa et al. ......... 356/237.4 |
| 7,123,356 B1 * | 10/2006 | Stokowski et al. ........ 356/237.2 |
| 2002/0019202 A1 * | 2/2002 | Thomas et al. ................ 451/57 |
| 2002/0038294 A1 * | 3/2002 | Matsugu ....................... 706/20 |
| 2002/0093647 A1 * | 7/2002 | Fukazawa et al. ......... 356/237.1 |
| 2002/0109110 A1 * | 8/2002 | Some et al. ............... 250/559.4 |
| 2004/0257571 A1 * | 12/2004 | Mieher et al. ................ 356/401 |
| 2007/0030773 A1 * | 2/2007 | Kuroda et al. ............ 369/44.31 |

\* cited by examiner

*Primary Examiner*—Tarifur R. Chowdhury
*Assistant Examiner*—Isiaka O Akanbi
(74) *Attorney, Agent, or Firm*—Ann Marie Mewherter

(57) ABSTRACT

Methods and systems for inspection of a wafer or setting up an inspection process are provided. One method for inspection of a wafer includes detecting first and second sets of defects on the wafer by performing different scans of the wafer with different focus offsets. The method also includes comparing results of the different scans for a defect of the first set and a defect of the second set that are detected at approximately the same location on the wafer. The method further includes determining if the defect of the first and second sets is a defect of an underlying layer or an uppermost layer formed on the wafer based on results of the comparing step.

29 Claims, 2 Drawing Sheets

METHODS AND SYSTEMS FOR INSPECTION OF A WAFER OR SETTING UP AN INSPECTION PROCESS

PRIORITY CLAIM

This application claims priority to U.S. Provisional Application No. 60/719,078 entitled "Methods and Systems for Inspection of a Wafer or Setting up an Inspection Process," filed Sep. 21, 2005, which is incorporated by reference as if fully set forth herein.

BACKGROUND OF THE INVENTION

1. Field of the Invention

This invention generally relates to methods and systems for inspection of a wafer or setting up an inspection process. Certain embodiments relate to detecting defects on a wafer at different focus offsets and determining if the defects are defects of an underlying layer or an uppermost layer formed on the wafer.

2. Description of the Related Art

The following description and examples are not admitted to be prior art by virtue of their inclusion in this section.

Inspection processes are used at various steps during a semiconductor manufacturing process to detect defects on wafers to promote higher yield in the manufacturing process and thus higher profits. Inspection has always been an important part of fabricating semiconductor devices such as integrated circuits. However, as the dimensions of semiconductor devices decrease, inspection becomes even more important to the successful manufacture of acceptable semiconductor devices because smaller defects can cause the device to fail. For instance, as the dimensions of semiconductor devices decrease, detection of defects of decreasing size has become necessary since even relatively small defects may cause unwanted aberrations in the semiconductor devices.

Inspection tools can be categorized generally according to their optical configuration. For instance, some inspection tools are configured to perform inspection using a brightfield configuration, and other inspection tools are configured to perform inspection using a darkfield configuration. In general, a brightfield configuration is used to detect light reflected specularly from a wafer. In contrast, a darkfield configuration is used to detect light scattered from a wafer. Therefore, depending on the characteristics of the wafer and the characteristics of the defects of interest, one configuration may be more suitable for inspection of the wafer than another.

The different configurations also have different constraints on their usefulness based on their performance characteristics such as sensitivity, resolution, throughput, number of nuisance defects detected, and the like. One such constraint on the usefulness of brightfield tools is the detection of defects of underlying layers on a wafer, which can dominate the inspection results and make analysis of the inspection results difficult. For instance, different inspections are typically performed on different levels of the wafer to understand the defects that occur at various process steps. Due to the transparency of the materials that are processed in some process steps, process variations and other defects at previous process levels may be detected during inspection of these materials. The detection of these process variations at previous process levels can overwhelm the resulting defect population and make separation of the current layer defect signals from the overall signals difficult. These problems have been a constant challenge to brightfield inspection.

Many different approaches have been tried to separate prior level events from current level events. Events can be generally defined as abnormalities on a wafer that may be defects. The terms "events" and "defects" are used interchangeably herein. One such approach involves inspecting the wafer after each level is formed and performing defect source analysis (DSA) of the results of both inspections. DSA generally includes analyzing inspected features and locations of defects on the same wafer at different points in time, or in the manufacturing process. Further description of DSA can be found in U.S. Pat. No. 5,991,699 to Kulkarni et al., which is incorporated by reference as if fully set forth herein. With this approach, inspection is performed at two different levels of the wafer such that the events that are common to the two processing steps (i.e., defects detected by both inspections) can be filtered out of the results for the current level.

However, the above-described method does have some drawbacks. For instance, DSA requires lot holding and inspection at prior levels that may not be critical layers in of themselves thereby resulting in lower productivity. In addition, coordinate inaccuracy between the two inspections may result in poor DSA results, lower prior level noise suppression, and/or missing current level defects. DSA also cannot be performed unless inspection results from the prior level are available.

Another approach involves using nuisance filtering algorithms to filter defects of previous levels from results of the inspection of a current level. This approach also has inherent drawbacks. For instance, the algorithms can only be used if there are distinguishable attribute differences between events of the previous level and events of the current level. Therefore, the application of this approach may be relatively limited.

Accordingly, it would be advantageous to develop methods and systems for inspection of a wafer that can be used to discriminate between defects of an underlying layer and defects of an uppermost layer formed on a wafer, that do not use results of previous inspection of the underlying layer thereby improving productivity, that are relatively insensitive to coordinate inaccuracy, and that can be used to distinguish between defects on different layers that may or may not have different attributes.

SUMMARY OF THE INVENTION

The following description of various embodiments of methods and systems is not to be construed in any way as limiting the subject matter of the appended claims.

One embodiment relates to a method for inspection of a wafer. The method includes detecting first and second sets of defects on the wafer by performing different scans of the wafer with different focus offsets. The method also includes comparing results of the different scans for a defect of the first set and a defect of the second set that are detected at approximately the same location on the wafer. In addition, the method includes determining if the defect of the first and second sets is a defect of an underlying layer or an uppermost layer formed on the wafer based on results of the comparing step.

In one embodiment, the different scans are performed after the uppermost layer has been formed on the wafer. In another embodiment, inspection of the underlying layer is not performed before the uppermost layer has been formed on the wafer. In some embodiments, the underlying layer is a non-critical layer of a device being fabricated on the wafer.

In an embodiment, the uppermost layer is at least partially transparent to a wavelength of light used for the different scans. In another embodiment, the different scans are performed using a brightfield technique. In an additional embodiment, the different scans are performed by a single inspection system in a single inspection process. In some embodiments, the different focus offsets include approximately best focus for defects of the underlying layer and approximately best focus for defects of the uppermost layer. In a further embodiment, parameters of the different scans other than the different focus offsets are substantially the same.

In one embodiment, the comparing step includes comparing a magnitude of the results of the different scans. In one such embodiment, the determining step includes determining if the magnitude increases or decreases from a first of the different scans to a second of the different scans. In another embodiment, the detecting step includes detecting the first and second sets of defects on the wafer by comparing the results of the different scans to the same threshold. In a further embodiment, the method includes removing the defect from results of the inspection if the defect is a defect of the underlying layer. Each of the steps of each of the embodiments of the method described above may be performed as described herein. Each of the embodiments of the method described above may include any other step(s) described herein.

Another embodiment relates to a method for setting up an inspection process. The method includes selecting first and second defects on the wafer. The first defects are known to be caused by a first process performed on the wafer. The second defects are known to be caused by a second process performed on the wafer. The first process is performed before the second process. The method also includes measuring one or more properties of the first and second defects at different focus offsets. In addition, the method includes selecting for use in the inspection process a pair of the different focus offsets. At least one of the one or more properties of the first and second defects change in opposite directions from a first focus offset of the pair to a second focus offset of the pair.

In one embodiment, the at least one of the one or more properties includes magnitude. In another embodiment, the method includes determining if defects detected on the wafer are the first defects or the second defects using scanning electron microscopy. Each of the steps of each of the embodiments of the method described above may be performed as described herein. Each of the embodiments of the method described above may include any other step(s) described herein.

An additional embodiment relates to a system configured to inspect a wafer. The system includes an optical subsystem configured to perform different scans of the wafer with different focus offsets. The system also includes a processor configured to detect first and second sets of defects on the wafer using results of the different scans. The processor is also configured to compare the results for a defect of the first set and a defect of the second set that are detected at approximately the same location on the wafer. In addition, the processor is configured to determine if the defect of the first and second sets is a defect of an underlying layer or an uppermost layer formed on the wafer based on results of the comparison.

In one embodiment, the uppermost layer is at least partially transparent to a wavelength of light used by the optical subsystem for the different scans. In another embodiment, the optical subsystem is configured to perform the different scans of the wafer in a single inspection process. In an additional embodiment, the optical subsystem is configured to perform the different scans using a brightfield technique. Although relatively high numerical aperture (NA) brightfield inspection may be a particularly suitable inspection mode for the systems described herein due to the relatively small depth of field (i.e., depth of focus), it is to be understood that the optical subsystem may be configured to perform the different scans using any appropriate technique known in the art.

In an embodiment, the different focus offsets include approximately best focus for defects of the underlying layer and approximately best focus for defects of the uppermost layer. In another embodiment, parameters of the optical subsystem during the different scans other than the different focus offsets are substantially the same.

In some embodiments, the results compared by the processor include a magnitude of the results of the different scans. In one such embodiment, the processor is configured to determine if the defect of the first and second sets is a defect of the underlying layer or the uppermost layer based on whether the magnitude increases or decreases from a first of the different scans to a second of the different scans. In another embodiment, the processor is configured to detect the first and second sets of defects by comparing the results of the different scans to the same threshold. In a further embodiment, the processor is configured to remove the defect from results of the inspection if the defect is a defect of the underlying layer. Each of the embodiments of the system described above may be further configured as described herein.

A further embodiment relates to a method for inspection of a wafer. This method includes detecting first and second sets of defects on the wafer using first and second inspection modes, respectively. The first inspection mode is sensitive to defects of an underlying layer formed on the wafer or defects of an uppermost layer formed on the wafer. The second inspection mode is sensitive to defects of the underlying layer and the uppermost layer. The method also includes comparing the first and second sets of defects as a function of location on the wafer. In addition, the method includes determining if defects of the first and second sets are defects of the underlying layer or the uppermost layer based on results of the comparing step.

In one embodiment, detecting the first and second sets of defects on the wafer using the first and second inspection modes, respectively, is performed simultaneously. In a different embodiment, detecting the first and second sets of defects on the wafer using the first and second inspection modes, respectively, is performed sequentially. In an additional embodiment, the first and second inspection modes are optical inspection modes. Each of the steps of each of the embodiments of the method described above may be performed as described herein. Each of the embodiments of the method described above may include any other step(s) described herein.

Another embodiment relates to a system configured to inspect a wafer. The system includes an optical subsystem configured to scan the wafer using first and second inspection modes. The first inspection mode is sensitive to defects of an underlying layer formed on the wafer or defects of an uppermost layer formed on the wafer. The second inspection mode is sensitive to defects of the underlying layer and the uppermost layer. The system also includes a processor configured to detect first and second sets of defects on the wafer using results of the scan using the first and second modes, respectively. The processor is also configured to compare the first and second sets of defects as a function of location on the wafer. In addition, the processor is configured to determine if defects of the first and second sets are defects of the underlying layer or the uppermost layer based on results of the comparison.

In one embodiment, the optical subsystem is configured to scan the wafer using the first and second inspection modes simultaneously. In another embodiment, the optical subsystem is configured to scan the wafer using the first and second modes sequentially. Each of the embodiments of the system described above may be further configured as described herein.

BRIEF DESCRIPTION OF THE DRAWINGS

Other objects and advantages of the invention will become apparent upon reading the following detailed description and upon reference to the accompanying drawings in which.

Figure 1:
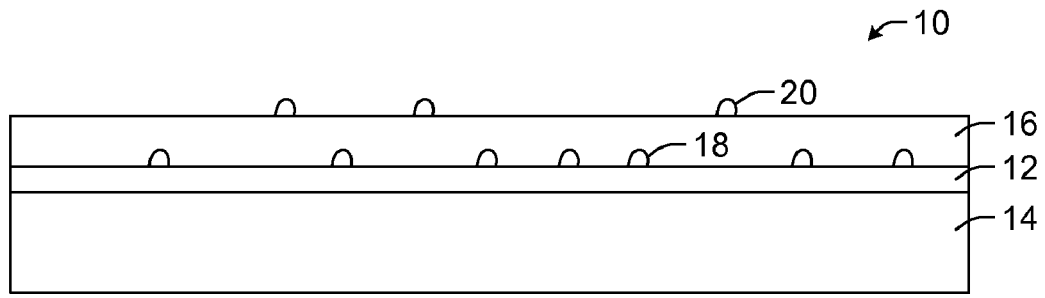
FIG. 1 is a schematic diagram illustrating a cross-sectional view of a wafer after an underlying layer and an uppermost layer have been formed on the wafer.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

A wafer may include one or more layers formed upon a substrate. For example, such layers may include, but are not limited to, a resist, a dielectric material, and a conductive material. Many different types of such layers are known in the art, and the term wafer as used herein is intended to encompass a wafer including all types of such layers.

One or more layers formed on a wafer may be patterned or unpatterned. For example, a wafer may include a plurality of dies, each having repeatable patterned features. Formation and processing of such layers of material may ultimately result in completed devices. Many different types of devices may be formed on a wafer, and the term wafer as used herein is intended to encompass a wafer on which any type of device known in the art is being fabricated.

Although the embodiments of the methods and systems are described herein with respect to a wafer, it is to be understood that the methods and systems described herein may be used for inspection or setting up an inspection process for any specimen that includes an uppermost layer that is at least partially transparent to a wavelength of light used for the inspection.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

FIG. 1 illustrates one example of a wafer that may be advantageously inspected using method and/or system embodiments described herein. As shown in FIG. 1, wafer 10 includes underlying layer 12 formed on substrate 14. Substrate 14 may be formed of a material as described above. Underlying layer 12 may be formed of any material that can be formed on substrate 14. Underlying layer 12 may be formed of, for example, an insulating material, a conductive material, or a semiconductive material. In one example, underlying layer 12 may be an epitaxial layer. Uppermost layer 16 is also formed on wafer 10. In particular, as shown in FIG. 1, uppermost layer 16 is formed upon and in contact with underlying layer 12. Uppermost layer 16 may be formed of, for example, a resist, an insulating material, a conductive material, or a semiconductive material. In one example, if underlying layer 12 is an epitaxial layer, uppermost layer 16 may be a gate dielectric layer.

Although underlying layer 12 and uppermost layer 16 are shown as non-patterned layers in FIG. 1, it is to be understood that one or more of these layers may be patterned. The underlying and uppermost layers may be formed and/or altered during any processes that can be used to form devices on a wafer. Processes that alter the layers on the wafer include, but are not limited to, ion implantation, chemical-mechanical polishing, etch, cleaning, and thermal processing. Formation of the layers may be performed using any suitable processes known in the art such as chemical vapor deposition, physical vapor deposition, atomic layer deposition, and plating.

In addition, although uppermost layer 16 is formed on wafer 10 after underlying layer 12 is formed on the wafer, additional layer(s) (not shown) may be formed between underlying layer 12 and uppermost layer 16. Additional layer(s) may also be formed between underlying layer 12 and substrate 14. In addition, inspection of the wafer is performed as described herein after formation and/or other processing of the uppermost layer. After inspection of the wafer, additional layers (not shown) may be formed on top of uppermost layer 16. In this manner, the terms "underlying" and "uppermost" are used herein to discriminate between two different layers formed on a wafer that have a particular spatial relationship with respect to each other. However, these terms may not accurately describe the spatial relationship of these layers with respect to other layers on the wafer at previous and subsequent process steps in device fabrication being performed on the wafer.

As further shown in FIG. 1, defects 18 may be formed on underlying layer 12. Defects 18 of underlying layer 12 may have been caused by the process level that involved formation and/or processing of underlying layer 12. Although defects 18 are all shown to be formed on an upper surface of underlying layer 12, defects (not shown) may also or alternatively be formed under the upper surface of underlying layer 12 (e.g., partially subsurface defects such as pits and scratches or completely subsurface defects such as voids).

Defects 20 may be formed on uppermost layer 16. Defects 20 of uppermost layer 16 may have been caused by the process level that involved formation and/or processing of uppermost layer 16. Although defects 20 are all shown to be formed on an upper surface of uppermost layer 16, defects (not shown) may also or alternatively be formed under the upper surface of uppermost layer 16 (e.g., partially subsurface defects such as pits and scratches or completely subsurface defects such as voids and inclusions).

Figure 2:
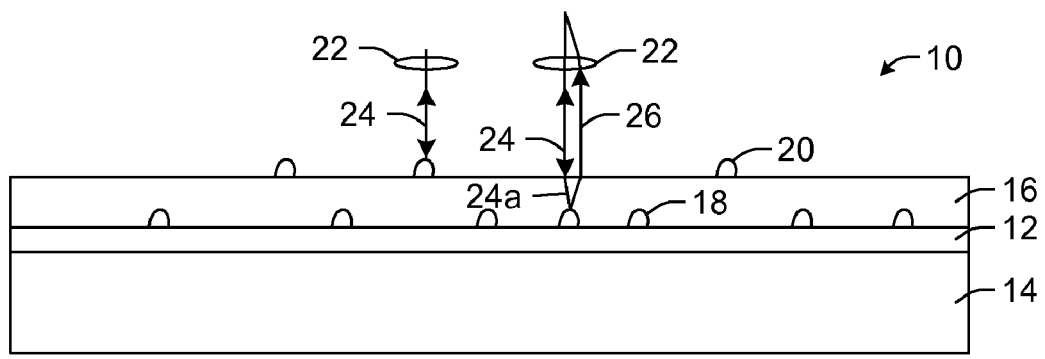
FIG. 2 is a schematic diagram illustrating a cross-sectional view of the wafer of FIG. 1 and light directed to and returned from the wafer during inspection of the wafer performed with only one focus offset.

If uppermost layer 16 is formed of a material that is at least partially transparent to a wavelength of light used during inspection, then defects 18 and 20 may both be detected during inspection of the uppermost layer. For instance, as shown in FIG. 2, inspection may involve focusing light 24 to wafer 10 and collecting light 24 reflected from wafer 10 using objective lens 22, which forms a part of the inspection system used for this inspection. Additional components of an inspection system that is configured for inspection of uppermost layer 16 are described further herein. Since the uppermost layer is the layer of interest in this inspection, the focal plane (not shown) of the inspection system may be arranged to be proximate to the upper surface of the uppermost layer. The location of the focal plane may be arranged prior to inspection and may be substantially constant during inspection. The focal plane may be arranged to be proximate to the upper surface of the uppermost layer to increase the signal-to-noise ratio of the light returned from the wafer thereby increasing the sensitivity of the system for detection of defects on the upper surface of the uppermost layer.

However, if the uppermost layer is at least partially transparent to a wavelength of the light used for inspection, then some of light 24 focused to wafer 10 will be transmitted through the uppermost layer. For instance, as shown in FIG. 2, light 24 may be directed to a focal plane (not shown) located proximate to an upper surface of the uppermost layer. Some of light 24 will be reflected from the upper surface of the uppermost layer. However, some of light 24 (light 24a) will also be transmitted through the uppermost layer. In particular, light 24a transmitted by the uppermost layer may be refracted through the uppermost layer and may be incident upon an upper surface of underlying layer 12 or a defect on the upper surface of the underlying layer.

The upper surface or a defect of underlying layer 12 may reflect, diffract, or scatter light 24a back through the uppermost layer. In this manner, light 26 returned from the upper surface or a defect of underlying layer 12 may be refracted back through the uppermost layer and collected by objective lens 22. Since the focal plane of the inspection system is located proximate to the upper surface of uppermost layer 16, the intensity of the light returned from the upper surface or a defect of underlying layer 12 may not be high in comparison to the light returned from the upper surface or a defect of uppermost layer 16. However, since the intensity of light returned from defects of uppermost layer 16 will vary depending upon, for example, characteristics of the defects, it will be impossible to determine if a defect signal detected during the inspection of uppermost layer 16 represents a defect of uppermost layer 16 or a defect of underlying layer 12 without further information about the defects of the underlying layer.

The embodiments of the methods and systems described herein, however, can be used to facilitate capture of defects from one process layer while suppressing the signal from another process layer. In other words, the method and system embodiments described herein achieve higher sensitivity to defects at the layer of interest by separating and/or eliminating events from a different layer.

Figure 3:
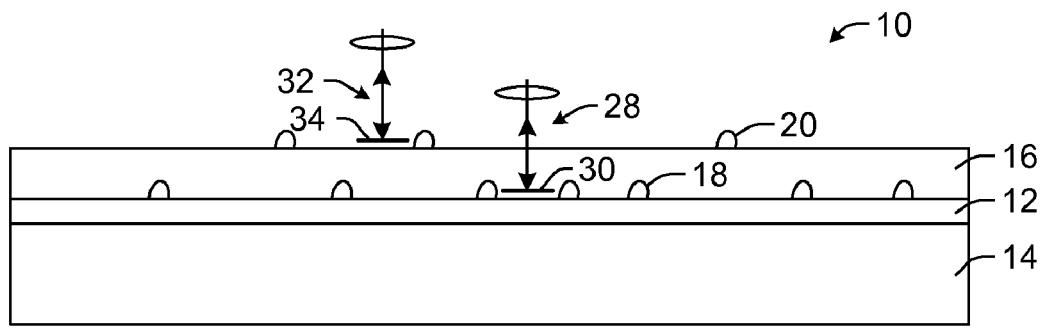
FIG. 3 is a schematic diagram illustrating a cross-sectional view of the wafer of FIG. 1 and light directed to and returned from the wafer during inspection of the wafer performed according to embodiments described herein.

One embodiment of a method for inspection of a wafer includes detecting first and second sets of defects on the wafer by performing different scans of the wafer with different focus offsets. The wafer may be configured as described above. As shown in FIG. 3, uppermost layer 16 may be at least partially transparent to a wavelength of light used for the different scans. For instance, uppermost layer 16 may be a gate dielectric layer, an oxide layer, a low-k dielectric layer, an interlevel dielectric (ILD) layer, or a pre-metal dielectric (PMD) layer. Obviously, uppermost layers that will benefit from inspection as described herein will vary depending on the wavelength(s) of the light used for inspection since most materials exhibit changes in transparency with changes in wavelength. The wavelength(s) of the light used for the different scans may be, for example, in the ultraviolet-visible (UV-Vis) range (e.g., wavelengths from about 200 nm to about 800 nm). The different focus offsets may be selected such that the focal planes of the different scans are located at different positions with respect to the uppermost layer and the underlying layer. In particular, due to the at least partial transparency of the uppermost layer to a wavelength used for inspection, one of the different focal planes of one of the different scans may be located under an upper surface of the uppermost layer (e.g., proximate to an upper surface of the underlying layer or closer to the upper surface of the underlying layer than the upper surface of the uppermost layer).

For example, as shown in FIG. 3, first scan 28 of wafer 10 may be performed with a first focus offset that results in a position of focal plane 30 that is proximate to an upper surface of underlying layer 12. As further shown in FIG. 3, second scan 32 of wafer 10 may be performed with a second focus offset that results in focal plane 34 being located proximate to an upper surface of uppermost layer 16. Since defects 18 and 20 are located proximate to the upper surfaces of underlying layer 12 and uppermost layer 16, respectively, the different focus offsets may be approximately best focus for defects of the underlying layer and approximately best focus for defects of the uppermost layer. However, in any embodiment regardless of the position of the defects, the different focus offsets may include approximately best focus for defects of the underlying layer and approximately best focus for defects of the uppermost layer. In other words, the focal planes of the different scans may or may not be located proximate to the upper surfaces of the layers. Instead, the focal planes are preferably located proximate to the defects of the different layers which may or may not be formed on the surfaces of the layers. Such different focus offsets may be determined experimentally as described further herein.

In some embodiments, parameters of the different scans other than the different focus offsets are substantially the same. For instance, the wavelength of light, the angle of incidence, the angle of collection, the detection system parameters, etc. may be the same for the different scans. In this manner, the only system parameter that is changed between the different scans is the focus offset thereby resulting in very little system adjustment and very little delay between the different scans. The focus offset may be altered between the different scans in any manner known in the art (e.g., changing the magnification of the lens of the inspection system). In addition, since the results of the different scans are used in combination to determine which defects are defects of the uppermost layer and which defects are defects of an underlying layer as described further herein, using system parameters other than focus offset that are substantially the same for the different scans reduces variations in the results of the different scans due to variations in the systems parameters other than focus offset thereby eliminating a potential source of error.

In one embodiment, the different scans are performed by a single inspection system in a single inspection process. In other words, wafer 10 may be disposed upon a stage (not shown) of an inspection system during both scans. In addition, the inspection system may perform the different scans of the wafer one after another (i.e., serially) in the single inspection process (e.g., without removing the wafer from the stage between the different scans). Therefore, the different scans of the wafer may be performed as individual tests of a single inspection process. Scanning of the wafer during the different scans may be performed in any suitable manner known in the art (e.g., moving optics of the inspection system while the wafer is stationary, moving (e.g., rotating and/or translating) the wafer while the optics of the inspection system are stationary, or moving the optics of the inspection system and the wafer). In additional embodiments, the different scans are performed using a brightfield technique. In this manner, the inspection system may perform the different scans by detecting light specularly reflected from the wafer. The inspection system may be further configured as described herein.

As described above, therefore, the different scans are performed after the uppermost layer has been formed on the wafer. The different scans may also or alternatively be performed after the uppermost layer has been processed or altered. In addition, inspection of the underlying layer may not be performed before the uppermost layer has been formed on the wafer. In this manner, unlike some of the previously used methods for discriminating between defects of different layers of a wafer, using the methods described herein, the wafer does not have to be scanned prior to formation of the uppermost layer. As such, the methods and systems described herein may be used to improve throughput and productivity of the fabrication process.

Such elimination of the inspection prior to formation of the uppermost layer may be particularly advantageous when defects of the underlying layer are not particularly of interest. For instance, in one embodiment, the underlying layer is a non-critical layer of a device being fabricated on the wafer. In this manner, unlike some previously used methods in which a previously formed layer on a wafer had to be inspected in order to differentiate between defects of different layers even if the previously formed layer was a non-critical layer, the methods and systems described herein allow inspection of underlying layers that would not normally be inspected to be eliminated thereby eliminating any non-yield related inspection and improving throughput and productivity compared to the previous methods and systems.

In one embodiment, the detecting step described above includes detecting the first and second sets of defects on the wafer by comparing the results of the different scans to the same threshold. Preferably, the threshold is sensitive to defects of interest in both scans of the inspection. In addition, any method, technique, and/or algorithm for detecting defects in results of a wafer scan may be used in the methods described herein. However, preferably the method, technique, and/or algorithm used in the methods described herein for detecting defects in the results of both of the different scans is sensitive to defects of interest in both scans. The locations of the defects on the wafer detected in the results of both scans may be determined in any manner known in the art (e.g., from wafer alignment information, scan path information, scanning rate information, etc.).

In some embodiments, the method includes performing Venn Analysis or any other commonality or comparison analysis known in the art on the results of the different scans to identify the defects that are common to both scans and have approximately the same location on the wafer. For instance, two wafer maps, each illustrating the results of one of the different scans, may be overlaid to identify defects detected in both scans that have approximately the same location on the wafer. It may be advantageous when determining if defects of the different scans have the same location to allow for some variation in the locations of the defects between the first and second sets that may result from, for example, variation in components of the system over time (e.g., due to vibration). However, the variation in the defect locations due to such variation in the system may be relatively low, particularly in comparison to the error in defect locations inherent in previously used inspection methods and systems that results from coordinate inaccuracy caused by change in position of the wafer on the stage between different scans that results from removing the wafer from the stage between the scans necessitated because the different scans were performed after different layers are formed on the wafer.

The method described above also includes comparing results of the different scans for a defect of the first set and a defect of the second set that are detected at approximately the same location on the wafer. The results that are compared in this step may include any measurement acquired during the scans that will vary depending on focus offset as described further below.

The method also includes determining if the defect of the first and second sets is a defect of an underlying layer or an uppermost layer formed on the wafer based on results of the comparing step. In particular, the defect may be determined to be a defect of an underlying layer or an uppermost layer formed on the wafer based on the change in the results from one scan to the next. For instance, the results may include magnitude of the defect signal, which will decrease as the focal plane is located farther away from the defect. Other such results include area of the defect signal, which will increase as the focal plane is located farther away from the defect. This variation in the area of the defect signal is similar to the smudging or blurring effect caused by the defect being out-of-focus.

In this manner, the magnitude of the defect signals for defects 18 will decrease from first scan 28 to second scan 32 since the focal plane of the inspection system moves away from defects 18 from the first scan to the second scan. In contrast, the magnitude of the defect signals for defects 20 will increase from first scan 28 to second scan 32 since the focal plane of the inspection system moves toward defects 20 from the first scan to the second scan. In one embodiment, therefore, the comparing step includes comparing a magnitude of the results of the different scans. In such an embodiment, the determining step includes determining if the magnitude increases or decreases from a first of the different scans to a second of the different scans. In other words, the determining step may include identifying the defects that have a change in magnitude between the two scans in a positive direction and identifying the defects that have a change in magnitude between the two scans in a negative direction.

Obviously, the first and second scans may be performed in any order. For instance, the first and second scans may be performed as described above, with the focal plane of the first scan located proximate to defects 18 of the underlying layer and with the focal plane of the second scan located proximate to defects 20 of the uppermost layer. In contrast, the focal plane of the first scan may be located proximate to defects 20 of the uppermost layer, and the focal plane of the second scan may be located proximate to defects 18 of the underlying layer. In such scanning, the trend of the changes in the results for defects 20 and defects 18 described above will be reversed. In particular, the magnitude of defects 20 will decrease from the first scan to the second scan while the magnitude of defects 18 will increase from the first scan to the second scan. In this manner, the different scans may be performed in any order as long as the focus offsets of the different scans are known such that different trends may be appropriately associated with different defects.

In some embodiments, the method includes removing the defect from results of the inspection if the defect is a defect of the underlying layer. In this manner, the method may include filtering defects that change in magnitude in the same manner as the previous layer defects. As such, the remaining defect population includes only the defects at the current layer. In other words, the results of the inspection may include only the defects of interest (i.e., defects of the uppermost layer). The results of the inspection may be reported, stored, etc. in any form known in the art such as a wafer map, a file, or a database.

The methods and systems described herein, therefore, provide more meaningful results to the user than currently used methods and systems since only the defects of interest are included in the inspection results. In this manner, the user may be able to more clearly evaluate the quality of the uppermost layer or the performance of the process used to fabricate the uppermost layer. In addition, further processing of the defects will be substantially easier and quicker since the inspection results include only the defects of interest. Such processing of the defects may include, for example, defect review, defect classification, defect analysis, etc. Furthermore, since the inspection results include only the defects of the uppermost layer, process monitoring performed using the inspection results may be much more accurate, and process control performed based on the inspection results may result in dramatically tighter control of the process thereby increasing yield and profits.

In summary, therefore, the methods described herein generally include performing two scans at the same process step. The first scan is performed at approximately best focus for the prior-level nuisance defects. The second scan is performed at approximately best focus for the current-level defects. The magnitude and/or dimensions of the detected events in both scans are compared. The magnitude of events from the previous layer will decrease from the first scan to the second scan. At the same time, the area of the events from the previous layer will increase from the first scan to the second scan. The reverse is true for an event occurring at the current layer of inspection. In particular, the difference between the higher magnitude pixel in the two above scans is a positive value for previous level defects. The difference between the magnitude for an event in the current layer will be a negative value. These differences can be used to separate the previous layer events from the current layer events. Each of the embodiments of the method described above may include any other step(s) described herein.

The embodiments of the method described above have a number of additional advantages over the currently used methods for discriminating between current layer and previous layer defects. For instance, the methods described herein eliminate the need for otherwise unnecessary inspections at prior steps. In addition, the methods described herein do not suffer from coordinate inaccuracy issues for events detected in previous layers. Furthermore, the methods described herein can be used to discriminate between previous layer and current layer defects irrespective of whether the events from the different layers have distinguishable attributes such as polarity or size. This insensitivity to defect attributes makes the methods described herein superior to known nuisance filtering algorithms, which rely on defect attributes to distinguish between defects of different layers.

The methods described herein also provide particular advantages for brightfield inspection. For instance, the prime technical gap of brightfield inspection is inundation of signal by events from previous processing steps. This detection of defects from previous processing steps limits the scope of adoption of brightfield inspection in many different process levels that are critical to yield control in semiconductor manufacturing. The detection of defects from previous processing steps also indicates that yield enhancement engineers lose sensitivity to possible critical defects at these inspection levels. The methods described herein will, however, bridge that gap thereby enabling the use of brightfield technology for inspection of some of the layers that have been considered to fall within the brightfield technology gap due to previous layer nuisance defect detection. This elimination of previous layer nuisance defect detection will in turn increase the utilization of brightfield inspection tools for inspection of additional levels of semiconductor fabrication.

Another embodiment of a method for inspection of a wafer includes detecting first and second sets of defects on the wafer using first and second inspection modes, respectively. The first inspection mode is sensitive to defects of an underlying layer formed on the wafer or defects of an uppermost layer formed on the wafer. In other words, the first inspection mode is sensitive to only one of the sets of defects. The second inspection mode is sensitive to defects of the underlying layer and the uppermost layer. In this manner, the second inspection mode is sensitive to both sets of defects. In addition, unlike other method embodiments described herein in which defects are detected using results different scans performed at different focus offsets, the first and second inspection modes may be performed at approximately the same focus offset.

The method also includes comparing the first and second sets of defects as a function of location on the wafer. For example, a defect detected using the first inspection mode may be compared to defects detected using the second inspection mode at approximately the location of the defect. In addition, the method includes determining if defects of the first and second sets are defects of the underlying layer or the uppermost layer based on results of the comparing step. In this manner, the defects which appear in the first set of defects can be used to determine which layer defects of the second set are located on. In one particular example, if the first inspection mode is sensitive to only defects of the underlying layer, then defects detected by the second inspection mode at approximately the same locations as defects detected by the first inspection mode may be identified as previous layer noise. These defects may then be eliminated from the second set of defects to arrive at a set of defects that contains only defects of the current or uppermost layer. As such, the methods described herein can be used to filter or "suppress" previous layer noise from inspection results.

In one embodiment, detecting the first and second sets of defects on the wafer using the first and second inspection modes, respectively, is performed simultaneously. In other words, the first and second inspection modes may be performed on the wafer in a single scan. In a different embodiment, detecting the first and second sets of defects on the wafer using the first and second inspection modes, respectively, is performed sequentially. In this manner, the first and second inspection modes may be performed on the wafer in different scans. The scans for the first and second inspection modes may be performed in any order. In one embodiment, the first and second inspection modes are optical inspection modes. For example, the first and second inspection modes may include brightfield inspection and darkfield inspection. However, any other suitable combination of optical inspection modes may be used in the methods described herein.

In another embodiment, one of the first and second inspection modes may be an optical inspection mode, and the other of the first and second inspection modes may be a non-optical inspection mode (e.g., an electron beam based inspection mode). For example, another option for detecting defects of uppermost layers, which are at least partially transparent, without detecting defects of previously formed layers is to use a scanning electron microscope (SEM) to detect defects of the uppermost layer. In particular, defects of previously formed layers will not be "visible" to the SEM. However, SEMs have dramatically lower throughput than optical inspection systems particularly for whole wafer inspection. Therefore, the methods described herein provide a viable solution to eliminate defects of previous layers that are visible on inspection systems, but not on SEMs. Obviously, some of the methods described herein may have a somewhat lower throughput than previously used inspection methods since some of the methods involve at least two scans of the wafer at different focus offsets. However, the lower throughput of such methods are thoroughly compensated for by the numerous advantages, including those described above, provided by the methods. Each of the embodiments of the method described above may include any other step(s) of any other method(s) described herein.

Another embodiment relates to a method for setting up an inspection process. In particular, the method can be used to set up an inspection process for an optical inspection system. This method may also be used to set up the inspection process that is used in the embodiments of the method described above for inspection of a wafer. In addition, this method may be used to set up different inspection processes for different device layers. Once an inspection process is set up for a device layer, the inspection process can generally be used for inspection of all other wafers on which the device layer is formed.

The first step in the method for setting up an inspection process may be to identify a combination of spectral wavelength(s) and pixel size that is sensitive to the defects of interest. The identification of a spectral mode and pixel size combination is standard in and central to brightfield inspection. If at the determined spectral wavelength(s) and pixel size, previous layer defects are captured with approximately the same magnitude as current layer defects, a focus evaluation may be performed.

For instance, the method includes selecting first and second defects on the wafer. The selected defects will be used in the focus evaluation. In general, two or more of each of the first and second defects may be selected for the focus evaluation. In this manner, the focus evaluation is performed on a few current layer defects and a few previous layer defects. The first defects are known to be caused by a first process performed on the wafer. The second defects are known to be caused by a second process performed on the wafer. The first process is performed before the second process. In this manner, the first defects are previous level defects or defects of an underlying layer while the second defects are current level defects or defects of an uppermost layer. The type(s) of defects that are selected for the focus evaluation (e.g., particles, pattern defects such as bridges, etc.) will not affect the results of the methods described herein. The defects that are selected for the focus evaluation may all be of the same type or of different types. In addition, the defects that are selected for the focus evaluation may or may not be killer defects or defects of interest.

In one embodiment, the method includes determining if defects detected on the wafer are the first defects or the second defects using scanning electron microscopy. In this manner, defect review may be performed using a SEM, after the first inspection with the spectral mode and pixel combination identified above, to identify defects of the current level and defects of the previous level. For instance, defects of the previous level and the current level will be detected by optical inspection if the uppermost layer is at least partially transparent to a selected spectral wavelength used in the optical inspection. However, defects of the previous level will not be visible to the SEM while defects of the current level are visible to the SEM. Therefore, the SEM can be used to discriminate between current level and previous level defects.

The method also includes measuring one or more properties of the first and second defects at different focus offsets. In particular, one or more properties of the first and second defects selected as described above may be measured in this step. In addition, the method includes selecting for use in the inspection process a pair of the different focus offsets at which at least one of the one or more properties of the first and second defects change in opposite directions from a first focus offset of the pair to a second focus offset of the pair.

In one embodiment, the at least one of the one or more properties measured at the different focus offsets includes signal-to-noise ratio. In such an embodiment, the focus evaluation may include the following steps. For instance, a signal-to-noise analysis may be performed at different focus offset steps (e.g., about 0.1 μm, 0.15 μm, etc.) across a range of focus values (e.g., about +1.0 μm to about −1.0 μm, about +2.0 μm to about −2.0 μm, etc.). The different focus offset steps and the range of focus values at which the analysis is performed may vary depending on, for example, the configuration of the inspection system (e.g., numerical aperture (NA), depth of focus, resolution capability, etc.) and possibly the characteristics of the wafer (e.g., thickness of the transparent layer, characteristics of the stack of layers formed on the wafer, etc.). At each focus offset step, the signal-to-noise ratio of the defects of interest and the previous layer defects is measured. The focus offset pair at which the signal-to-noise ratio for the defects of interest changes in the opposite direction to changes in the signal-to-noise ratio of the previous layer defects may then be identified. At the identified focus offsets, a full wafer inspection may then be performed as described above. Each of the embodiments of the method described above may include any other step(s) described herein.

Existing software capabilities can be used to facilitate the focus evaluation. In addition, a system such as that described further herein can be configured such that the system matrices the difference in signal-to-noise ratio with each focus offset pair for each candidate defect. The system may also be configured to manipulate the matrix to identify the focus offset combination that separates the magnitude of the two defect types in opposite directions. Once the focus offset combination is identified as described above, an inspection can be performed at these focus offsets as described above. Defects that are common to the two scans at the different focus offsets can be identified. The system may further be configured to compare the magnitude of the defects from the two scans and filter out the previous layer defects from defects of interest based on opposite trends of magnitude variation to complete the nuisance filtering paradigm.

Figure 4:
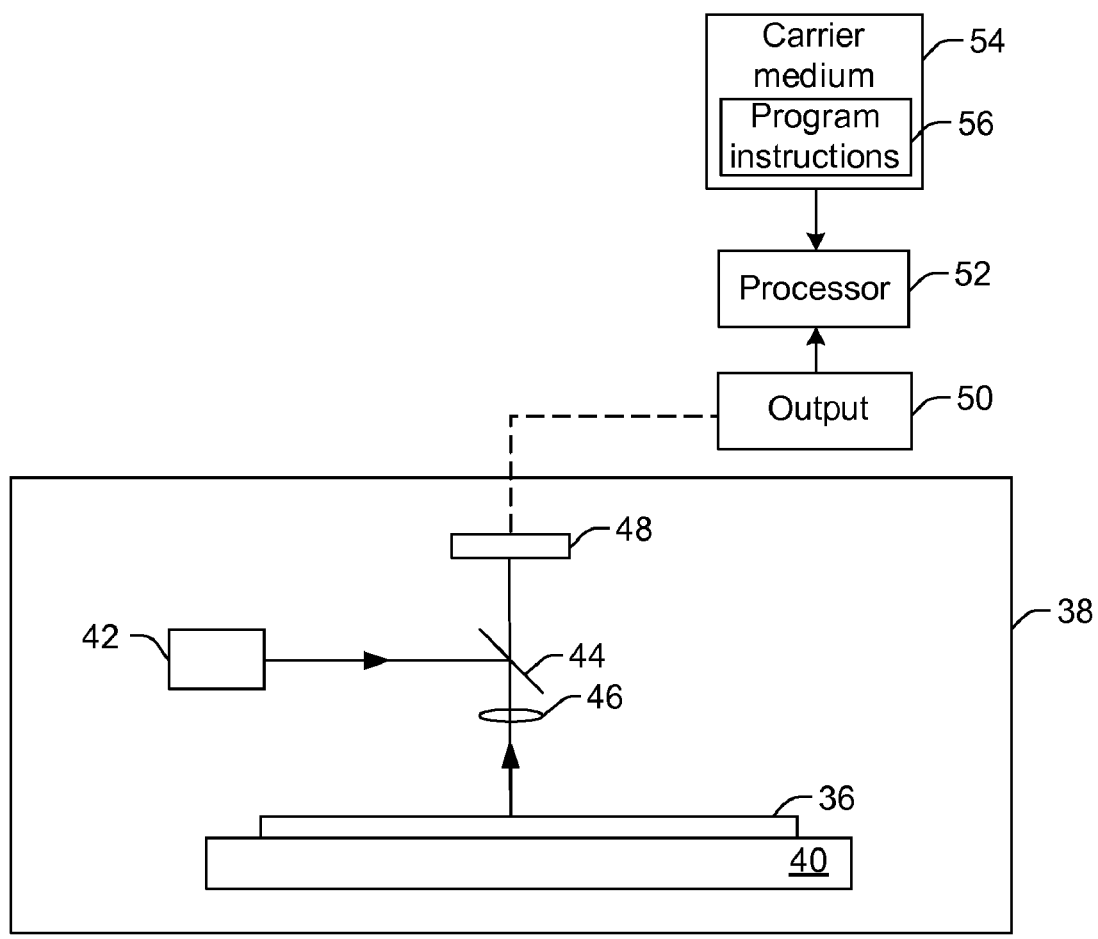
FIG. 4 is a schematic diagram illustrating a side view of one embodiment of a system configured to inspect a wafer.

FIG. 4 illustrates one embodiment of a system configured to inspect wafer 36. Wafer 36 may include an uppermost layer (not shown in FIG. 4) and an underlying layer (not shown in FIG. 4), which may be configured as described further above and shown in FIG. 1. The system includes optical subsystem 38 that is configured to perform different scans of wafer 36 with different focus offsets. In some embodiments, the uppermost layer formed on the wafer is at least partially transparent to a wavelength of light used by the optical subsystem for the different scans. As described further above, in one embodiment, the different focus offsets include approximately best focus for defects of the underlying layer and approximately best focus for defects of the uppermost layer.

The system may also include stage 40 on which wafer 36 may be disposed during the different scans. In this manner, the different scans are performed on wafer 36 while the wafer is disposed on the same stage. In other words, the wafer is not removed from the stage between the different scans. In this manner, the optical subsystem is configured to perform the different scans of the wafer in a single inspection process. The different scans of the wafer may be performed as different tests of the same inspection process. Stage 40 may include any suitable mechanical or robotic assembly known in the art. Scanning of the wafer may be performed by moving the optical subsystem while the wafer is stationary, moving (e.g., translating and/or rotating) the wafer while the optical subsystem is stationary, or moving the optical subsystem and the wafer simultaneously.

Optical subsystem 38 includes light source 42. Light source 42 may include any suitable light source known in the art. In addition, light source 42 may be configured to emit light having any suitable wavelength(s) known in the art. For example, light generated by light source 42 may include light having one or more wavelengths in the UV-Vis range. Light generated by light source 42 is directed by beamsplitter 44 to objective lens 46. As shown in FIG. 4, beamsplitter 44 and objective lens 46 may be configured to direct the light to the wafer at a substantially normal angle of incidence.

Light specularly reflected from wafer 36 is collected by objective lens 46. In this manner, optical subsystem 38 is configured to perform the different scans of the wafer using a brightfield technique. In addition, the focus offset of the optical subsystem may be altered between the different scans by changing the magnification of objective lens 46. In some embodiments, parameters of optical subsystem 38 during the different scans other than the different focus offsets are substantially the same.

Light collected by objective lens 46 is directed through beamsplitter 44 to detector 48. Detector 48 may include any suitable detector known in the art such as a photomultiplier tube (PMT) or a charge coupled device (CCD) camera. Detector 48 is configured to generate output 50 in response to the light reflected from the wafer and collected by objective lens 46.

The system shown in FIG. 4 also includes processor 52. Processor 52 may be configured to receive output 50 from detector 48. For instance, processor 52 may be coupled to the detector by a transmission medium (not shown). The transmission medium may include any suitable transmission medium known in the art. In addition, processor 52 may be coupled to the detector by one or more components (not shown) interposed between the detector and the processor such as an analog-to-digital converter or any other suitable components known in the art.

Processor 52 is configured to detect first and second sets of defects on the wafer using results of the different scans. The processor may be configured to detect the first and second sets of defects on the wafer as described further above. For instance, in one embodiment, the processor is configured to detect the first and second sets of defects by comparing the results of the different scans to the same threshold.

The processor is also configured to compare the results for a defect of the first set and a defect of the second set that are detected at approximately the same location on the wafer. In one embodiment, the results compared by the processor include a magnitude of the different scans (e.g., the magnitude of the defects of the first and second sets detected at approximately the same location on the wafer). The processor may be configured to compare these and any other results of the different scans as described further above.

In addition, the processor is configured to determine if the defect of the first and second sets is a defect of an underlying layer or an uppermost layer formed on wafer 36 based on results of the comparison. In one embodiment, the processor is configured to determine if the defect of the first and second sets is a defect of the underlying layer or a defect of the uppermost layer based on whether the magnitude increases or decreases from a first of the different scans to a second of the different scans. Such a determination may be performed as described further above.

The processor may be configured to perform any other step(s) of any of the method(s) described herein. For instance, the processor may be configured to remove the defect from results of the inspection if the defect is a defect of the underlying layer. In addition, the processor may be configured to perform one or more steps of the embodiments of a method for setting up an inspection process described further above.

Processor 52 may take various forms, including a personal computer system, mainframe computer system, workstation, image computer, parallel processor, or any other device known in the art. In general, the term "computer system" may be broadly defined to encompass any device having one or more processors, which executes instructions from a memory medium.

The system shown in FIG. 4 may also include carrier medium 54. Program instructions for implementing methods such as those described herein may be transmitted over or stored on the carrier medium. In particular, carrier medium 54 includes program instructions 56 executable on processor 52 for performing one or more steps of the methods described herein. The carrier medium may be a transmission medium such as a wire, cable, or wireless transmission link. The carrier medium may also be a storage medium such as a read-only memory, a random access memory, a magnetic or image acquisition disk, or a magnetic tape.

The program instructions may be implemented in any of various ways, including procedure-based techniques, component-based techniques, and/or object-oriented techniques, among others. For example, the program instructions may be implemented using Matlab, Visual Basic, ActiveX controls, C, C++ objects, C#, JavaBeans, Microsoft Foundation Classes ("MFC"), or other technologies or methodologies, as desired.

Although one particular configuration of a system is shown in FIG. 4, it is to be understood that the methods described herein may be performed using any system that can scan a wafer with different focus offsets. In addition, the system may include any optical subsystem that is configured to inspect a wafer with a wavelength of light to which an uppermost layer on the wafer is at least partially transparent. Furthermore, the system may include any optical subsystem that is configured to inspect the wafer using a brightfield technique. Examples of other inspection systems that may be configured to perform the methods described herein include, but are not limited to, the 23xx family of tools that are commercially available from KLA-Tencor, San Jose, Calif.

In another embodiment, a different system configured to inspect a wafer includes optical subsystem 38. Optical subsystem 38 is configured to scan wafer 36 using first and second inspection modes. The first inspection mode is sensitive to defects of an underlying layer formed on the wafer or defects of an uppermost layer formed on the wafer. In other words, the first inspection mode is sensitive to only one of the sets of defects or defects on only one of the layers on the wafer. The second inspection mode is sensitive to defects of the underlying layer and the uppermost layer. In this manner, the second inspection mode is sensitive to both sets of defects or defects on both layers. In addition, unlike other embodiments described herein in which defects are detected by different scans performed at different focus offsets, optical subsystem 38 may be configured to scan wafer 36 using first and second inspection modes at approximately the same focus offset. In one example, the optical subsystem may be configured for first and second inspection modes such as brightfield inspection and dark field inspection. For example, the optical subsystem may include an additional detector (not shown) configured to detect light scattered from wafer 36. However, the optical subsystem may be configured to perform any other suitable combination of optical inspection modes that may exhibit different sensitivity to defects on multiple layers of a wafer.

In one embodiment, the optical subsystem is configured to scan the wafer using the first and second inspection modes simultaneously. In other words, the optical subsystem may be configured to inspect the wafer using the first and second inspection modes in a single scan of the wafer. In a different embodiment, the optical subsystem is configured to scan the wafer using the first and second inspection modes sequentially. In this manner, the optical subsystem may be configured to perform the first and second inspection modes on the wafer in different scans. In such embodiments, the scans for the first and second inspection modes may be performed on the wafer in any order by the optical subsystem.

Such a system also includes processor 52 configured to detect first and second sets of defects on the wafer using results of the scan using the first and second modes, respectively. Processor 52 is also configured to compare the first and second sets of defects as a function of location on the wafer and to determine if defects of the first and second sets are defects of the underlying layer or the uppermost layer based on results of the comparison. For example, the processor may be configured to compare a defect detected by the first inspection mode to defects detected by the second inspection mode at approximately the location of the defect detected by the first inspection mode. In this manner, defects that appear in the first set of defects can be used to determine which layer defects of the second set are located on. In one particular example, if the first inspection mode is sensitive to only defects of the underlying layer, then defects detected by the second inspection mode at approximately the same locations as defects detected by the first inspection mode may be identified as previous layer defects and noise. The processor may also be configured to eliminate these defects from the second set of defects to thereby produce a set of defects that contains only the defects of the current or uppermost layer. As such, the systems described herein can be used to filter or "suppress" previous layer noise from the inspection results. The processor may be configured to perform each of these steps as described further herein. In addition, processor 52 included in these embodiments may be further configured as described herein.

As described above, the first and second inspection modes may be optical inspection modes. However, in other embodiments, the first and second inspection modes may include optical and non-optical inspection modes. For example, optical subsystem 38 may be configured to perform one of the first and second inspection modes. The other of the first and second inspection modes may be performed using a non-optical inspection subsystem (not shown) such as an electron beam inspection subsystem. Such a non-optical inspection subsystem may be included in the system shown in FIG. 4 (e.g., in the same or different measurement chamber (not shown) of optical subsystem 38). In this embodiment, defects of the current layer will be detected by the non-optical inspection subsystem, and defects of the previous layer will not be detected by the non-optical inspection subsystem. In this manner, defects that do not appear at approximately the same location in both the results of the optical inspection and the results of the non-optical inspection may be identified as previous layer defects. Each of the embodiments of this system may be further configured as described herein.

In some embodiments, the systems described herein may be configured as "stand alone tools" or tools that are not physically coupled to a process tool. However, such a system may be coupled to the process tool (not shown) by a transmission medium, which may include wired and wireless portions. The process tool may include any process tool known in the art such as a lithography tool, an etch tool, a deposition tool, a polishing tool, a plating tool, a cleaning tool, or an ion implantation tool. The process tool may be configured as a cluster tool or a number of process modules coupled by a common handler.

The results of the inspection performed by the methods and systems described herein may be used to alter a parameter of a process or a process tool using a feedback control technique, a feedforward control technique, and/or an in situ control technique. The parameter of the process or the process tool may be altered manually or automatically.

Further modifications and alternative embodiments of various aspects of the invention may be apparent to those skilled in the art in view of this description. For example, methods and systems for inspection of a wafer or setting up an inspection process are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

The invention claimed is:

1. A method for inspection of a wafer, comprising:
 detecting first and second sets of defects on the wafer by performing different scans of the wafer with different focus offsets;
 comparing results of the different scans for a defect of the first set and a defect of the second set that are detected at approximately the same location on the wafer;
 determining if the defect of the first and second sets is a defect of an underlying layer or an uppermost layer formed on the wafer based on results of said comparing; and
 removing the defect from results of the inspection if the defect is a defect of the underlying layer.

2. The method of claim 1, wherein the different scans are performed after the uppermost layer has been formed on the wafer.

3. The method of claim 1, wherein inspection of the underlying layer is not performed before the uppermost layer has been formed on the wafer.

4. The method of claim 1, wherein the underlying layer is a non-critical layer of a device being fabricated on the wafer.

5. The method of claim 1, wherein the uppermost layer is at least partially transparent to a wavelength of light used for the different scans.

6. The method of claim 1, wherein the different scans are performed using a brightfield technique.

7. The method of claim 1, wherein the different scans are performed by a single inspection system in a single inspection process.

8. The method of claim 1, wherein the different focus offsets comprise approximately best focus for defects of the underlying layer and approximately best focus for defects of the uppermost layer.

9. The method of claim 1, wherein parameters of the different scans other than the different focus offsets are substantially the same.

10. The method of claim 1, wherein said comparing comprises comparing a magnitude of the results of the different scans, and wherein said determining comprises determining if the magnitude increases or decreases from a first of the different scans to a second of the different scans.

11. The method of claim 1, wherein said detecting comprises detecting the first and second sets of defects on the wafer by comparing the results of the different scans to the same threshold.

12. A method for setting up an inspection process, comprising:
selecting first and second defects on the wafer, wherein the first defects are known to be caused by a first process performed on the wafer, wherein the second defects are known to be caused by a second process performed on the wafer, and wherein the first process is performed before the second process;
measuring one or more properties of the first and second defects at different focus offsets of an inspection system used in the inspection process; and
selecting for use in the inspection process a pair of the different focus offsets, wherein at least one of the one or more properties of the first and second defects change in opposite directions from a first focus offset of the pair to a second focus offset of the pair.

13. The method of claim 12, wherein the at least one of the one or more properties comprises magnitude.

14. The method of claim 12, further comprising determining if defects detected on the wafer are the first defects or the second defects using scanning electron microscopy.

15. A system configured to inspect a wafer, comprising:
an optical subsystem configured to perform different scans of the wafer with different focus offsets; and
a processor configured to detect first and second sets of defects on the wafer using results of the different scans, to compare the results for a defect of the first set and a defect of the second set that are detected at approximately the same location on the wafer, to determine if the defect of the first and second sets is a defect of an underlying layer or an uppermost layer formed on the wafer based on results of the comparison, and to remove the defect from results of the inspection if the defect is a defect of the underlying layer.

16. The system of claim 15, wherein the uppermost layer is at least partially transparent to a wavelength of light used by the optical subsystem for the different scans.

17. The system of claim 15, wherein the optical subsystem is further configured to perform the different scans of the wafer in a single inspection process.

18. The system of claim 15, wherein the optical subsystem is further configured to perform the different scans using a brightfield technique.

19. The system of claim 15, wherein the different focus offsets comprise approximately best focus for defects of the underlying layer and approximately best focus for defects of the uppermost layer.

20. The system of claim 15, wherein parameters of the optical subsystem during the different scans other than the different focus offsets are substantially the same.

21. The system of claim 15, wherein the results compared by the processor comprise a magnitude of the results of the different scans, and wherein the processor is further configured to determine if the defect of the first and second sets is a defect of the underlying layer or the uppermost layer based on whether the magnitude increases or decreases from a first of the different scans to a second of the different scans.

22. The system of claim 15, wherein the processor is further configured to detect the first and second sets of defects by comparing the results of the different scans to the same threshold.

23. A method for inspection of a wafer, comprising:
detecting first and second sets of defects on the wafer using first and second inspection modes, respectively, wherein the first inspection mode is sensitive to defects of an underlying layer formed on the wafer or defects of an uppermost layer formed on the wafer, and wherein the second inspection mode is sensitive to defects of the underlying layer and the uppermost layer;
comparing the first and second sets of defects as a function of location on the wafer;
determining if defects of the first and second sets are defects of the underlying layer or the uppermost layer based on results of said comparing; and
removing the defects from results of the inspection if the defects are defects of the underlying layer.

24. The method of claim 23, wherein said detecting using the first and second inspection modes is performed simultaneously.

25. The method of claim 23, wherein said detecting using the first and second inspection modes is performed sequentially.

26. The method of claim 23, wherein the first and second inspection modes are optical inspection modes.

27. A system configured to inspect a wafer, comprising:
an optical subsystem configured to scan the wafer using first and second inspection modes, wherein the first inspection mode is sensitive to defects of an underlying layer formed on the wafer or defects of an uppermost layer formed on the wafer, and wherein the second inspection mode is sensitive to defects of the underlying layer and the uppermost layer; and
a processor configured to detect first and second sets of defects on the wafer using results of the scan using the first and second modes, respectively, to compare the first and second sets of defects as a function of location on the wafer, to determine if defects of the first and second sets are defects of the underlying layer or the uppermost layer based on results of the comparison, and to remove the defects from results of the inspection if the defects are defects of the underlying layer.

28. The system of claim 27, wherein the optical subsystem is further configured to scan the wafer using the first and second inspection modes simultaneously.

29. The system of claim 27, wherein the optical subsystem is further configured to scan the wafer using the first and second inspection modes sequentially.

* * * * *

UNITED STATES PATENT AND TRADEMARK OFFICE
CERTIFICATE OF CORRECTION

PATENT NO. : 7,659,975 B1 Page 1 of 1
APPLICATION NO. : 11/533079
DATED : February 9, 2010
INVENTOR(S) : Ramani et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 410 days.

Signed and Sealed this

Thirtieth Day of November, 2010

David J. Kappos
*Director of the United States Patent and Trademark Office*